United States Patent
Mikhailov et al.

(10) Patent No.: US 9,399,911 B2
(45) Date of Patent: Jul. 26, 2016

(54) METHOD FOR DETERMINING WEIGHT CONCENTRATION OF CLAY IN A SAMPLE OF A POROUS MEDIUM

(71) Applicant: SCHLUMBERGER TECHNOLOGY CORPORATION, Sugar Land, TX (US)

(72) Inventors: Dmitry Mikhailov, Moscow (RU); Valery Vasilievich Shako, Moscow (RU); Evgeny Chuvilin, Moscow (RU); Tatiyana Buida, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 386 days.

(21) Appl. No.: 14/015,930

(22) Filed: Aug. 30, 2013

(65) Prior Publication Data

US 2014/0060172 A1 Mar. 6, 2014

(30) Foreign Application Priority Data

Sep. 3, 2012 (RU) ................................. 2012137223

(51) Int. Cl.
*E21B 49/02* (2006.01)
*G01N 33/28* (2006.01)
*G01N 15/08* (2006.01)

(52) U.S. Cl.
CPC .............. *E21B 49/02* (2013.01); *G01N 15/082* (2013.01); *G01N 33/2823* (2013.01); *G01N 2015/0833* (2013.01)

(58) Field of Classification Search
CPC .. E21B 49/02; G01N 15/082; G01N 33/2823; G01N 2015/0833
See application file for complete search history.

(56) References Cited

U.S. PATENT DOCUMENTS

| | | | |
|---|---|---|---|
| 4,495,292 A * | 1/1985 | Siebert | G01N 33/24 175/50 |
| 4,540,882 A | 9/1985 | Vinegar et al. | |
| 4,722,095 A | 1/1988 | Muegge et al. | |
| 5,027,379 A | 6/1991 | Hunt et al. | |
| 5,253,719 A | 10/1993 | Blauch et al. | |
| 6,009,747 A | 1/2000 | dos Santos | |
| 7,264,777 B1 * | 9/2007 | Blum | B01J 20/12 422/68.1 |
| 7,589,050 B2 | 9/2009 | Frenier et al. | |
| 2008/0280001 A1 * | 11/2008 | Sohling | B01J 2/28 426/531 |
| 2010/0094035 A1 * | 4/2010 | Ortiz Niembro | B01J 20/12 554/193 |

FOREIGN PATENT DOCUMENTS

GB 1250186 10/1971

* cited by examiner

*Primary Examiner* — John Fitzgerald
*Assistant Examiner* — Michael E Turbyfill

(57) ABSTRACT

For the purpose of determining a weight concentration of a clay material in a porous medium sample, a specific active surface area of the clay material and an initial specific active surface area of the porous sample are measured. A water solution of the clay material is pumped through the sample and a specific active surface area of the sample of the porous medium is measured after the pumping. Then, the weight concentration $n_{en}$ of the clay material is calculated.

2 Claims, 1 Drawing Sheet

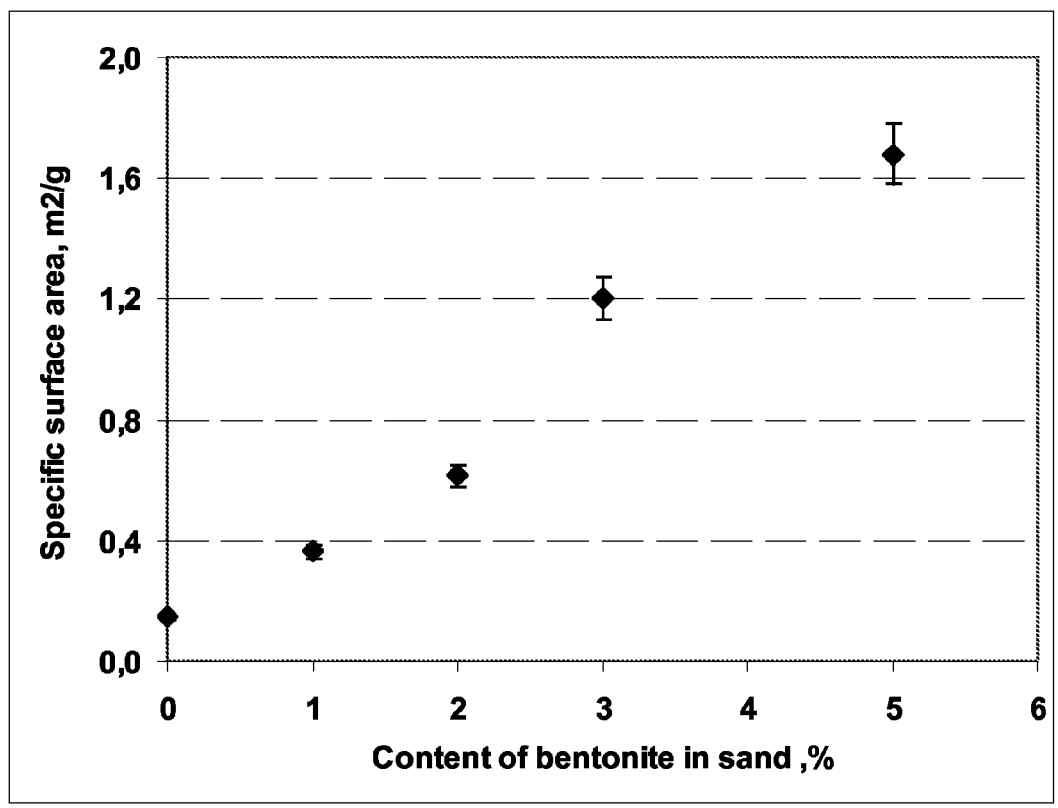

METHOD FOR DETERMINING WEIGHT CONCENTRATION OF CLAY IN A SAMPLE OF A POROUS MEDIUM

CROSS-REFERENCE TO RELATED APPLICATION

This application claims priority to Russian Application No. 2012137223 filed Sep. 3, 2012, which is incorporated herein by reference in its entirety.

BACKGROUND

The problem of formation damage under the impact of a drilling mud (or a flush liquid) is highly important, particularly in the case of long horizontal wells because most horizontal wells are completed without casing, i.e., without production string cementing and perforating.

Drilling mud is a complex mix of clay, fine particles (from several millimeters to less than one micron), and organic additives (polymers, surfactants, etc.) contained in a "carrying" fluid (a mud base). Such a base fluid could be water, oil, or some synthetic fluid.

While drilling, mud filtrate together with fine particles and clay contained therein may penetrate the formation near a well bore under excess pressure caising a considerable permeability reduction in the affected area. This phenomenon is commonly referred to as "damage of the formation nearwelbore area" or simply "formation damade."

During a well clean-up technological procedure (gradual transfer to the production mode) these components are partially washed out of the mud damaged zone, which facilitates its permeability repairing. However, some of those components remain captured in the rock pore space (adsorption on the pore surface, capture in pore throats, etc.), which results in a significant difference between the initial permeability and the repaired permeability following the well clean-up procedure (the repaired permeability would normally represent about 50% to 70% of the initial permeability).

A laboratory method commonly used to control drilling mud quality is a filtration experiment in which the drilling mud is injected into a core sample with subsequent flowback (i.e., the displacement of the drilling mud in the sample by an original formation fluid), in which process measures are taken of permeability reduction/repairing as a function of the amount of fluid pore volumes (drill mud or formation fluid).

However, information on concentrations of clay and other mud components captured in the pore space after the mud has been displaced is important for understanding a mechanism behind formation damage and identifying an appropriate method for improving production index of well (minimizing the mud damaged zone). The conventional quality control method of the drilling mud referred to above envisions no such measurements.

Quantitative analysis of the formation damage mechanism associated with the penetration of clay materials while drilling is of the highest interest in view of the wide use of clay-based drilling muds. For instance, the Russian Federation National Standard ГОСТ 25795-83 recommends bentonite clays for drill mud preparation.

Weight concentration of drilling mud clay penetrating the pore space is typically small (no more than 1% or 1.5% by weight). Nonetheless, with a high swelling factor of clay and its porosity, even such a small weight concentration results in a significant reduction of rock permeability (5 to 20 times down).

The technical challenge is related to the fact that small weight concentrations of clay in a porous medium are hard to measure because X-ray diffraction and X-ray micro-computed tomography methods fail to provide sufficient resolution for weight concentrations of less than 1%.

U.S. Pat. Nos. 4,540,882 and 5,027,379 disclose methods for determining drill mud penetration depth using X-ray micro-computed tomography of core samples with a contrast agent added thereto. However, the use of a contrast agent dissolved in the "carrying" fluid does not provide determination of penetration and concentrations of clay and other weak-contrast admixtures contained in the drilling mud because the drill mud filtrate penetration depth generally differs from that of the said admixtures.

U.S. Pat. No. 5,253,719 offers a method for identification of formation damage mechanism through analysing radial-oriented core samples taken from the well. Core samples are analyzed with the help of various analytical methods identifying the type and extent of formation damage and depth of the mud-damaged zone. The analytical methods used include a X-Ray Diffraction (XRD) method, a Local X-Ray Spectral Analysis, Scanning Electron Microscopy (SEM), Back-Scattering Electron Microscopy, Petrography Analysis, and Optical Microscopy.

SUMMARY

Various embodiments of the invention provide for measuring small weight concentrations of clay material entering pore space while clay-containing fluid is injected.

The method for determining weight concentration of clay materials comprises the following processes: measuring a specific active surface area of a clay material and an initial specific active surface area of a porous sample, pumping a water solution of the clay material through the sample, measuring the specific active surface area of the porous sample after the pumping, and calculating weight concentration of clay material $n_{clay}$ in the porous sample as $$n_{clay} = \frac{S_\Sigma^s - S_0^s}{S_{clay}^s - S_0^s}$$

where $S_\Sigma^s$ is the specific active surface area of the porous sample after the pumping of the water solution with clay material, $S_0^s$ is the initial specific active surface area of the porous sample, and $S_{clay}^s$ is the specific active surface area of the clay material.

Before measuring the specific active surface area of the porous sample and after pumping the clay material water solution through the sample, the sample may be dried.

Various embodiments of the present invention can be used for nondestructive testing of porous materials. Specifically, the invention can be used for quantitative analysis of property deterioration of oil and gas bearing formations (formation damage) resulting from penetration of clay materials contained in a drilling mud.

BRIEF DESCRIPTION OF DRAWINGS

The invention is illustrated by:

FIG. 1 shows the dependence of specific active surface area of bentonite clay/fine sand fraction mixtures on clay content (by mass).

DETAILED DESCRIPTION

The physical basis of the above method is an additive increasing a specific active surface area of a porous sample with the increasing of clay content (by mass) in its pore space:

$$S_\Sigma^s m_\Sigma = S_0^s m_0 + S_{clay}^s m_{clay} \quad (1)$$

where $m_0$ and $S_0^s$ are mass and a specific active surface area of a porous sample before exposure to a clay material water solution; $m_{clay}$ and $S_{clay}^s$ are mass and specific active surface area of clay used for preparing the clay material water solution; $m_\Sigma$ and $S_\Sigma^s$ are mass and the specific active surface area of the porous sample after exposure to the clay material water solution.

Combining equation (1) with the mass balance:

$$m_\Sigma = m_0 + m_{clay}, \quad (2)$$

a weight concentration of clay $n_{clay}$ in the sample may be obtained with known $S_0^s$, $S_{clay}^s$ and $S_\Sigma^s$:

$$n_{clay} = \frac{S_\Sigma^s - S_0^s}{S_{clay}^s - S_0^s}, \text{ where } n_{clay} = \frac{m_{clay}}{m_\Sigma} \quad (3)$$

Considering that clay is characterized by high specific active surface area, the presence of even small clay content in pores results in a sharp increase of specific active surface area of the porous sample.

A series of special metrological experiments were conducted to measure specific active surface area of bentonite clay/fine sand fraction mixtures to verify the additivity of increasing a specific active surface area of the mixture with an increase in clay content (by mass).

Using a conventional nitrogen sorption method based on the Brunauer-Emmett-Teller (BET) Theory (See for instance, O. M. Poltorak, Thermodynamics in Physical Chemistry, M, Higher School, 1991, Pages 172-176), specific active surface area of the bentonite clay was measured, as well as specific active surface area of sand fines. A mixture of fine sand fraction and bentonite clay was prepared with a preset weight concentration of clay. Using the same nitrogen sorption method (BET), specific active surface area was measured of the said bentonite clay/fine sand fraction mixture. The measurements were repeated for bentonite clay/fine sand fraction mixtures with various weight concentrations of clay. The experimentally obtained values of specific active surface of bentonite clay/fine sand fraction mixtures with various clay content (by mass) are shown in FIG. 1. The experimental data allow for good approximation by linear dependence, which confirms the additivity of increasing the specific active surface area.

As an example, the invention was used to determine weight concentration of bentonite clay penetrating a porous sample, while pumping 1% solution of said clay through that sample.

The conventional nitrogen sorption method based on the BET theory was used to measure a specific active surface area of bentonite clay: $S_{clay}^s = 32.85 \text{ m}^2/\text{g}$ and 1% water solution of that clay was prepared (which is close to clay concentration in actual drilling muds) with a sodium salt additive (18 g/l).

The conventional nitrogen sorption method based on the BET theory was used to measure an initial specific active surface area of a porous material sample before pumping a clay-containing solution through the sample:

$$S_0^s = 1.27 \text{ m}^2/\text{g}$$

After that, the prepared 1% clay solution was pumped through that porous sample. A total of seven pore volumes (ratio of pumped solution volume to pore space volume of the sample) were pumped through following which filtration actually stopped because of considerable permeability reduction. At that point, the experiment stopped.

The porous sample was dried up and the specific active surface area of the same porous sample was measured by the conventional nitrogen sorption method based on the BET theory after seven pore volumes of 1% clay solution had been pumped through the sample:

$$S_\Sigma^s = 1.38 \text{ m}^2/\text{g}$$

Using equation (3) and the values of specific active surface areas of clay measured at earlier stages as well as those of the porous sample before and after pumping the clay-containing solution, weight concentration was calculated of the bentonite clay which penetrated into the porous sample:

$$n_{clay} \approx 0.35\%$$

The invention claimed is:

1. A method for determining a weight concentration of a clay material in a sample of a porous medium, the method comprising:
measuring a specific active surface area of the clay material and an initial specific active surface area of the sample of the porous medium,
pumping a water solution of the clay material through the sample of the porous medium,
measuring the specific active surface area of the sample of the porous medium after the pumping, and
calculating the weight concentration $n_{clay}$ of the clay material in the sample of the porous medium as $$n_{clay} = \frac{S_\Sigma^s - S_0^s}{S_{clay}^s - S_0^s}$$

where $S_\Sigma^s$ the specific active surface area of the sample of the porous medium after the pumping of the water solution of the clay material, $S_0^s$ is the initial specific active surface area of the sample of the porous medium, and $S_{clay}^s$ is the specific active surface area of the clay material.

2. The method of claim 1, wherein the sample of the porous medium is dried before measuring specific active surface area of the sample after pumping the water solution of the clay material through the sample.

* * * * *